(12) United States Patent
Axford et al.

(10) Patent No.: US 7,678,826 B2
(45) Date of Patent: Mar. 16, 2010

(54) ORGANIC COMPOUNDS FOR THE TREATMENT OF INFLAMMATORY OR ALLERGIC CONDITIONS

(76) Inventors: Jake Axford, Novartis Horsham Research Centre, Wimblehurst Road, West Sussex, Horsham (GB) RH12 5AB; Urs Baettig, Novartis Horsham Research Centre, Wimblehurst Road, West Sussex, Horsham (GB) RH12 5AB; Brian Cox, Novartis Horsham Research Centre, Wimblehurst Road, West Sussex, Horsham (GB) RH12 5AB; Kamlesh Jagdis Bala, Novartis Horsham Research Centre, Wimblehurst Road, West Sussex, Horsham (GB) RH12 5AB; Catherine LeBlanc, Novartis Horsham Research Centre, Wimblehurst Road, West Sussex, Horsham (GB) RH12 5AB; David Andrew Sandham, Novartis Horsham Research Centre, Wimblehurst Road, West Sussex, Horsham (GB) RH12 5AB ( * ) Notice: Subject to any disclaimer, the term of this patent is extended or adjusted under 35 U.S.C. 154(b) by 0 days.

(21) Appl. No.: 11/915,168

(22) PCT Filed: May 22, 2006

(86) PCT No.: PCT/EP2006/004851
§ 371 (c)(1),
(2), (4) Date: Nov. 21, 2007

(87) PCT Pub. No.: WO2006/125596
PCT Pub. Date: Nov. 30, 2006

(65) Prior Publication Data
US 2008/0200466 A1 Aug. 21, 2008

(30) Foreign Application Priority Data
May 24, 2005 (GB) .................................. 0510584.6

(51) Int. Cl.
*A01N 43/36* (2006.01)
(52) U.S. Cl. .................... 514/423; 514/237.5; 514/330; 514/255.01; 548/540; 544/106; 544/391; 546/226
(58) Field of Classification Search ............. 514/237.5, 514/423, 330, 255.01; 548/540; 544/106, 544/391; 546/226
See application file for complete search history.

(56) References Cited

U.S. PATENT DOCUMENTS

2004/0220237 A1* 11/2004 Fu et al. ...................... 514/357

FOREIGN PATENT DOCUMENTS

| WO | WO 2004/089885 | * | 10/2004 |
| WO | WO 2004/089885 A1 | | 10/2004 |

* cited by examiner

*Primary Examiner*—Kamal A Saeed
*Assistant Examiner*—Valerie Rodriguez-Garcia
(74) *Attorney, Agent, or Firm*—Mark Milstead; Vinit Kathardekar

(57) ABSTRACT

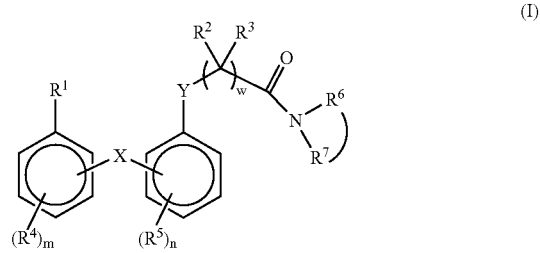

Compounds of formula (I) in free or pharmaceutically acceptable salt form, where $R^1$, $R^2$, $R^3$, $R^4$, $R^5$, $R^6$, $R^7$, m, n, w, X, and Y have the meanings as indicated in the specification, are useful for treating conditions mediated by the $CRTh_2$ receptor, especially inflammatory or obstructive airways diseases.

7 Claims, No Drawings

ORGANIC COMPOUNDS FOR THE TREATMENT OF INFLAMMATORY OR ALLERGIC CONDITIONS

This application is a US National Phase filing of PCT/EP2006/004851 filed May 22, 2006, the contents of which are incorporated herein by reference.

The present invention relates to organic compounds, their preparation and their use as pharmaceuticals.

In a first aspect, the present invention provides compounds of formula (I)

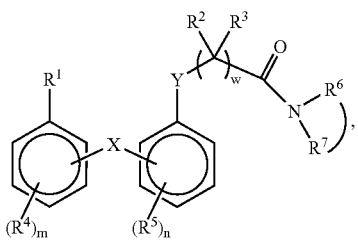

in free or pharmaceutically acceptable salt form, wherein
$R^1$ is selected from $R^{1a}S-$, $R^{1a}O-$ and $R^{1a}NR^9-$, wherein $R^{1a}$ is

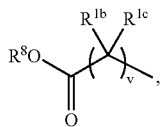

wherein
- $R^{1b}$ and $R^{1c}$ are independently selected from H, $C_1$-$C_8$-alkyl, and together with the carbon atom to which they are attached form a divalent $C_3$-$C_8$-cycloaliphatic group;
- $R^2$ and $R^3$ are independently selected from H, $C_1$-$C_8$-alkyl, and together with the carbon atom to which they are attached form a divalent $C_3$-$C_8$-cycloaliphatic group;
- $R^4$ and $R^5$ are independently selected from H, halogen, $C_1$-$C_8$-alkyl, $C_1$-$C_8$-haloalkyl, a $C_3$-$C_{15}$-carbocyclic group, nitro, cyano, $SO_2R^{5a}$, $C_1$-$C_8$-alkylcarbonyl, $C_1$-$C_8$-alkoxycarbonyl, $C_1$-$C_8$-alkoxy, $C_1$-$C_8$-haloalkoxy, $-SR^{5b}$, carboxy, carboxy-$C_1$-$C_8$-alkyl, amino, amino($C_1$-$C_8$-alkyl), $C_1$-$C_8$-alkylamino($C_1$-$C_8$-alkyl), di($C_1$-$C_8$-alkyl)amino($C_1$-$C_8$-alkyl), $C_1$-$C_8$-alkylamino, di($C_1$-$C_8$-alkyl)amino, $SO_2NR^{5c}R^{5d}$, $-C(O)NR^{5e}R^{5f}$, $C_1$-$C_8$-hydroxyalkyl, $NR^{5g}SO_2R^{5h}$, $NR^{5i}(CO)R^{5j}$, $SOR^{5k}$, a $C_6$-$C_{15}$-aromatic carbocyclic group and a 4- to 10-membered heterocyclic group having one or more heteroatoms selected from the group consisting of oxygen, nitrogen and sulphur;
- $R^{5a}$, $R^{5k}$ and $R^{5b}$ are independently selected from $C_1$-$C_8$-alkyl, $C_1$-$C_8$-hydroxyalkyl, $C_1$-$C_8$-alkylamino($C_1$-$C_8$-alkyl), di($C_1$-$C_8$-alkyl)amino($C_1$-$C_8$-alkyl), $C_1$-$C_8$-cyanoalkyl, a $C_3$-$C_{15}$-carbocyclic group, $C_1$-$C_8$-haloalkyl and a 4- to 10-membered heterocyclic group having one or more heteroatoms selected from the group consisting of oxygen, nitrogen and sulphur;
- $R^{5c}$, $R^{5d}$, $R^{5e}$ and $R^{5f}$ are, independently, H, $C_1$-$C_8$-alkyl, $C_1$-$C_8$-hydroxyalkyl, $C_1$-$C_8$-alkylamino($C_1$-$C_8$-alkyl), di($C_1$-$C_8$-alkyl)amino($C_1$-$C_8$-alkyl), $C_1$-$C_8$-cyanoalkyl, a $C_3$-$C_{15}$-carbocyclic group, $C_1$-$C_8$-haloalkyl, a 4- to 10-membered heterocyclic group having one or more heteroatoms selected from the group consisting of oxygen, nitrogen and sulphur, or, together with the nitrogen atom to which they are attached, form a $C_4$-$C_{10}$-heterocyclic group;
- $R^{5g}$ and $R^{5i}$ are independently selected from H, $C_1$-$C_8$-alkyl, $C_1$-$C_8$-hydroxyalkyl, $C_1$-$C_8$-alkylamino($C_1$-$C_8$-alkyl), di($C_1$-$C_8$-alkyl)amino($C_1$-$C_8$-alkyl), $C_1$-$C_8$-cyanoalkyl, a $C_3$-$C_{15}$-carbocyclic group, $C_1$-$C_8$-haloalkyl and a 4- to 10-membered heterocyclic group having one or more heteroatoms selected from the group consisting of oxygen, nitrogen and sulphur;
- $R^{5h}$ and $R^{5j}$ are independently selected from $C_1$-$C_8$-alkyl, a $C_3$-$C_{15}$-carbocyclic group, a 4- to 10-membered heterocyclic group having one or more heteroatoms selected from the group consisting of oxygen, nitrogen and sulphur, $C_1$-$C_8$-hydroxyalkyl, amino($C_1$-$C_8$-alkyl), $C_1$-$C_8$-alkylamino($C_1$-$C_8$-alkyl), di($C_1$-$C_8$-alkyl)amino($C_1$-$C_8$-alkyl) and $C_1$-$C_8$-cyanoalkyl;
- $R^6$ and $R^7$, together with the nitrogen to which they are attached, form a 4- to 10-membered heterocyclic group containing the indicated nitrogen atom as a ring heteroatom and optionally at least one ring heteroatom selected from the group consisting of nitrogen, oxygen and sulphur;
- $R^8$ is selected from H, $C_1$-$C_8$-alkyl, $C_3$-$C_{15}$-cycloalkyl, $C_1$-$C_8$-alkyl($C_6$-$C_{15}$-aromatic carbocyclic group) and $C_6$-$C_{15}$-aromatic carbocyclic group;
- $R^9$ is selected from H, $C_1$-$C_8$-alkyl, $C_3$-$C_{15}$-cycloalkyl, $C_1$-$C_8$-alkyl($C_6$-$C_{15}$-aromatic carbocyclic group) and $C_6$-$C_{15}$-aromatic carbocyclic group;
- X is $-CH_2-$, $-CH(C_1$-$C_8$-alkyl)-, $-CO-$, $-CH(OH)-$, $-CH(OC_1$-$C_8$-alkyl)-, $-C(halogen)_2-$, $-O-$, $-S-$, $-SO-$, $-SO_2-$ or a bond;
- Y is $-O-$, $-S-$, $-CH_2-$ or $-NR^7(C_1$-$C_8$-alkyl)-;
- m and n are each, independently, an integer selected from 0-3;
- v is an integer selected from 1-3; and
- w is an integer selected from 0-3.

According to formula (I), $R^1$ is $R^{1a}O-$, where $R^{1a}$ is

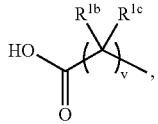

and $R^{1b}$ and $R^{1c}$ are H.

According to formula (I), $R^2$ and $R^3$ are, independently, H or $C_1$-$C_8$-alky, e.g. methyl.

According to formula (I), $R^6$ and $R^7$, together with the nitrogen to which they are attached, form a 4- to 10-membered heterocyclic group containing the indicated nitrogen atom as a ring heteroatom and optionally at least one ring heteroatom selected from the group consisting of nitrogen, oxygen and sulphur, which ring is unsubstituted or substituted by $C_1$-$C_4$-alkyl, e.g. methyl, cyano-$C_1$-$C_4$-alkyl, $C_1$-$C_8$-alkylamino or di($C_1$-$C_8$-alkylamino). Examples of the 4- to 10-membered heterocyclic group include, but are not limited to, a pyrrolidine ring, a morpholine ring, a piperazine ring, and a piperidine ring. Where the 4- to 10-membered heterocyclic group is a piperazine ring the piperazine ring is suitably substituted by methyl or a propionitrile group.

According to formula (I), $R^{12}$ and $R^{13}$ are, independently, H, or halogen.

According to formula (I), X is suitably —$CH_2$—, —S—, —SO— or —$SO_2$—.

According to formula (I), Y is suitably —O—;

According to formula (I), v is 1;

According to formula (I), w is an integer selected from 0-3.

Another embodiment of the present invention provides compounds, in free or pharmaceutically acceptable salt form, wherein the compound is of formula (Ia)

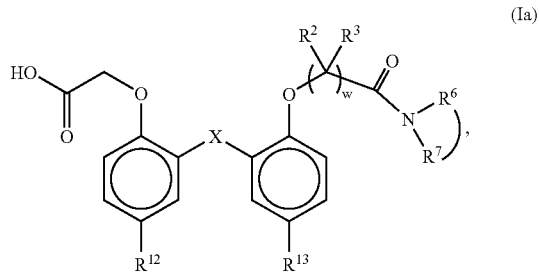

(Ia)

wherein $R^2$ and $R^3$ are, independently, H or $C_1$-$C_8$-alkyl;

$R^6$ and $R^7$, together with the nitrogen to which they are attached, form a 4- to 10-membered heterocyclic group containing the indicated nitrogen atom as a ring heteroatom and optionally at least one ring heteroatom selected from the group consisting of nitrogen, oxygen and sulphur, which ring is unsubstituted or substituted by $C_1$-$C_4$-alkyl or cyano-$C_1$-$C_4$-alkyl;

X is —$CH_2$—, —S—, —SO— or —$SO_2$—, preferably —$CH_2$—.

$R^{12}$ and $R^{13}$ are, independently, H, or halogen; and w is 1.

In another embodiment, the present invention provides for the use of a compound of formula (I) in any of the aforementioned embodiments, in free or pharmaceutically acceptable salt form, for the manufacture of a medicament for the treatment of an inflammatory or allergic condition, particularly an inflammatory or obstructive airways disease.

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

Definitions

Terms used in the specification have the following meanings:

"Optionally substituted", as used herein, means the group referred to can be substituted at one or more positions by any one or any combination of the radicals listed thereafter.

"Halogen" or "halo" may be fluorine, chlorine, bromine or iodine; preferably it is bromine or chlorine or fluorine.

"$C_1$-$C_8$-Alkyl" denotes straight-chain or branched $C_1$-$C_8$-alkyl, which may be, e.g., methyl, ethyl, n-propyl, isopropyl, n-butyl, isobutyl, sec-butyl, tert-butyl, straight- or branched-pentyl, straight- or branched-hexyl, straight- or branched-heptyl or straight- or branched-octyl. Preferably, $C_1$-$C_8$-alkyl is $C_1$-$C_4$-alkyl.

"$C_3$-$C_{15}$-Carbocyclic group", as used herein, denotes a carbocyclic group having 3- to 15-ring carbon atoms, e.g., a monocyclic group, either cycloaliphatic, such as a $C_3$-$C_8$- cycloalkyl, e.g., cyclopropyl, cyclobutyl, cyclopentyl, cyclohexyl, cycloheptyl or cyclooctyl; or aromatic, such as phenyl; or a bicyclic group, such as bicyclooctyl, bicyclononyl including indanyl and indenyl, and bicyclodecyl including naphthyl. Preferably, the $C_3$-$C_{15}$-carbocyclic group is a $C_3$-$C_{10}$-carbocyclic group, e.g., phenyl or naphthyl. The $C_3$-$C_{15}$-carbocyclic group can be substituted with 1-3 substituents or unsubstituted. Preferred substituents include halo, cyano, amino, nitro, carboxy, $C_1$-$C_8$-alkyl, $C_1$-$C_8$-haloalkyl, $C_1$-$C_8$-alkoxy, $C_1$-$C_8$-alkylcarbonyl, $C_1$-$C_8$-alkoxycarbonyl, $C_1$-$C_8$-haloalkoxy, carboxy-$C_1$-$C_8$-alkyl, $C_1$-$C_8$-alkylamino, di($C_1$-$C_8$-alkylamino), $C_1$-$C_8$-alkylsulfonyl, —$SO_2NH_2$, ($C_1$-$C_8$-alkylamino)sulfonyl, di($C_1$-$C_8$-alkyl)aminosulfonyl, aminocarbonyl, $C_1$-$C_8$-alkylaminocarbonyl and di($C_1$-$C_8$-alkyl)aminocarbonyl, a $C_3$-$C_{10}$-carbocyclic group and a 5- to 12-membered heterocyclic group having at least one ring heteroatom selected from nitrogen, oxygen and sulphur.

"$C_6$-$C_{15}$-Aromatic carbocyclic group", as used herein, denotes a divalent aromatic group having 6- to 15-ring carbon atoms, e.g., phenylene, naphthylene or anthrylene. The $C_6$-$C_{15}$-aromatic group can be substituted with 1-3 substituents or can be unsubstituted. Preferred substituents include halo, cyano, amino, nitro, carboxy, $C_1$-$C_8$-alkyl, halo-$C_1$-$C_8$-alkyl, $C_1$-$C_8$-alkoxy, $C_1$-$C_8$-alkylcarbonyl, $C_1$-$C_8$-alkoxycarbonyl, $C_1$-$C_8$-haloalkoxy, carboxy-$C_1$-$C_8$-alkyl, $C_1$-$C_8$-alkylamino, di($C_1$-$C_8$-alkylamino), $C_1$-$C_8$-alkylsulfonyl, —$SO_2NH_2$, ($C_1$-$C_8$-alkylamino)sulfonyl, di($C_1$-$C_8$-alkyl)aminosulfonyl, aminocarbonyl, $C_1$-$C_8$-alkylaminocarbonyl and di($C_1$-$C_8$-alkyl)aminocarbonyl, a $C_3$-$C_{15}$-carbocyclic group and a 5- to 12-membered heterocyclic group having at least one ring heteroatom selected from nitrogen, oxygen and sulphur.

"Divalent $C_3$-$C_8$-cycloaliphatic" denotes cycloalkylene having 3- to 8-ring carbon atoms, e.g., a monocyclic group, such as a cyclopropylene, cyclobutylene, cyclopentylene, cyclohexylene, cycloheptylene or cyclooctylene, any of which can be substituted by one or more, usually one or two, $C_1$-$C_4$-alkyl groups; or a bicyclic group, such as bicycloheptylene or bicyclooctylene. Preferably "$C_3$-$C_8$-cycloalkylene" is $C_3$-$C_5$-cycloalkylene, e.g., cyclopropylene, cyclobutylene or cyclopentylene.

"$C_1$-$C_8$-Alkoxy" denotes straight-chain or branched $C_1$-$C_8$-alkoxy which may be, e.g., methoxy, ethoxy, n-propoxy, isopropoxy, n-butoxy, isobutoxy, sec-butoxy, tert-butoxy, straight- or branched-pentoxy, straight- or branched-hexyloxy, straight- or branched-heptyloxy or straight- or branched-octyloxy. Preferably, $C_1$-$C_8$-alkoxy is $C_1$-$C_4$-alkoxy.

"$C_1$-$C_8$-Haloalkyl" and "$C_1$-$C_8$-haloalkoxy" denote $C_1$-$C_8$-alkyl and $C_1$-$C_8$-alkoxy, as hereinbefore defined, substituted by one or more halogen atoms, preferably one, two or three halogen atoms, preferably fluorine, bromine or chlorine atoms. Preferably, $C_1$-$C_8$-haloalkyl is $C_1$-$C_4$-alkyl substituted by one, two or three fluorine, bromine or chlorine atoms. Preferably, $C_1$-$C_8$-haloalkoxy is $C_1$-$C_4$-alkoxy substituted by one, two or three fluorine, bromine or chlorine atoms.

"$C_1$-$C_8$-Alkylsulfonyl", as used herein, denotes $C_1$-$C_8$-alkyl, as hereinbefore defined, linked to —$SO_2$—. Preferably, $C_1$-$C_8$-alkylsulfonyl is $C_1$-$C_4$-alkylsulfonyl, especially methylsulfonyl.

"Amino-$C_1$-$C_8$-alkyl" and "amino-$C_1$-$C_8$-alkoxy" denote amino attached by a nitrogen atom to $C_1$-$C_8$-alkyl, e.g., $NH_2$—($C_1$-$C_8$)—, or to $C_1$-$C_8$-alkoxy, e.g., $NH_2$—($C_1$-$C_8$)—O—, respectively, as hereinbefore defined. Preferably, amino-$C_1$-$C_8$-alkyl and amino-$C_1$-$C_8$-alkoxy are, respectively, amino-$C_1$-$C_4$-alkyl and amino-$C_1$-$C_4$-alkoxy.

"Amino-(hydroxy)-$C_1$-$C_8$-alkyl" denotes amino attached by a nitrogen atom to $C_1$-$C_8$-alkyl and hydroxy attached by an oxygen atom to the same $C_1$-$C_8$-alkyl. Preferably, amino-(hydroxy)-$C_1$-$C_8$-alkyl is amino-(hydroxy)-$C_2$-$C_4$-alkyl.

"Carboxy-$C_1$-$C_8$-alkyl" and "carboxy-$C_1$-$C_8$-alkoxy" denote carboxy attached by a carbon atom to $C_1$-$C_8$-alkyl or $C_1$-$C_8$-alkoxy, respectively, as hereinbefore defined. Preferably, carboxy-$C_1$-$C_8$-alkyl and carboxy-$C_1$-$C_8$-alkoxy are, respectively, carboxy-$C_1$-$C_4$-alkyl and carboxy-$C_1$-$C_4$-alkoxy.

"$C_1$-$C_8$-Alkylcarbonyl", "$C_1$-$C_8$-alkoxycarbonyl" and "$C_1$-$C_8$-haloalkylcarbonyl" denote $C_1$-$C_8$-alkyl, $C_1$-$C_8$-alkoxy or $C_1$-$C_8$-haloalkyl, respectively, as hereinbefore defined, attached by a carbon atom to a carbonyl group. "$C_1$-$C_8$-Alkoxycarbonyl" denotes $C_1$-$C_8$-alkoxy, as hereinbefore defined, wherein the oxygen of the alkoxy group is attached to the carbonyl carbon. Preferably, $C_1$-$C_8$-alkylcarbonyl, $C_1$-$C_8$-alkoxycarbonyl and $C_1$-$C_8$-haloalkylcarbonyl are, respectively, $C_1$-$C_4$-alkylcarbonyl, $C_1$-$C_4$-alkoxycarbonyl and $C_1$-$C_4$-haloalkylcarbonyl.

"$C_1$-$C_8$-Alkylamino" and "di($C_1$-$C_8$-alkyl)amino" denote $C_1$-$C_8$-alkyl, as hereinbefore defined, attached by a carbon atom to an amino group. The $C_1$-$C_8$-alkyl groups in di($C_1$-$C_8$-alkyl)amino may be the same or different. Preferably, $C_1$-$C_8$-alkylamino and di($C_1$-$C_8$-alkyl)amino are, respectively, $C_1$-$C_4$-alkylamino and di($C_1$-$C_4$-alkyl)amino.

"$C_1$-$C_8$-Alkylaminocarbonyl" and "di($C_1$-$C_8$-alkyl)aminocarbonyl" denote $C_1$-$C_8$-alkylamino and di($C_1$-$C_8$-alkyl)amino, respectively, as hereinbefore defined, attached by a nitrogen atom to the carbon atom of a carbonyl group. Preferably, $C_1$-$C_8$-alkylaminocarbonyl and di($C_1$-$C_8$-alkyl)-aminocarbonyl are, respectively, $C_1$-$C_4$-alkylaminocarbonyl and di($C_1$-$C_4$-alkyl)-aminocarbonyl.

As used herein, the term "4- to 10-membered heterocyclic group" is intended to mean a stable monocyclic or bicyclic heterocyclic ring which is saturated, partially unsaturated or unsaturated (aromatic), and which consists of at least one ring heteroatom selected from the group consisting of nitrogen, oxygen and sulphur, e.g., furan, tetrahydrofuran, pyrrole, pyrrolidine, pyrazole, imidazole, triazole, isotriazole, tetrazole, thiadiazole, isothiazole, oxadiazole, pyridine, oxazole, isoxazole, pyrazine, pyridazine, pyrimidine, piperidine, piperazine, morpholine, thiomorpholine, triazine, oxazine, thiazole, quinoline, isoquinoline, benzothiophene, benzoxazole, benzisoxazole, benzothiazole, benzisothiazole, benzofuran, indole, indazole or benzimidazole. Preferred heterocyclic groups include piperazine, morpholine, thiomorpholine, imidazole, isotriazole, pyrazole, pyridine, pyrrolidine, furan, oxazole, oxadiazole, isoxazole, thiazole, tetrazole benzothiophene, benzoxazole, benzothiazole and benzofuran. The 4- to 10-membered heterocyclic group can be unsubstituted or substituted. Preferred substituents include halo, cyano, oxo, hydroxy, carboxy, nitro, $C_1$-$C_8$-alkyl optionally substituted by cyano, $C_1$-$C_8$-alkylcarbonyl, hydroxy-$C_1$-$C_8$-alkyl, $C_1$-$C_8$-haloalkyl, amino-$C_1$-$C_8$-alkyl, $C_1$-$C_8$-alkylamino, di($C_1$-$C_8$-alkyl)amino amino(hydroxy)$C_1$-$C_8$-alkyl and $C_1$-$C_8$-alkoxy optionally substituted by aminocarbonyl. Especially preferred substituents include halo, oxo, $C_1$-$C_4$-alkyl, $C_1$-$C_4$-alkylcarbonyl, hydroxy-$C_1$-$C_4$-alkyl, $C_1$-$C_4$-haloalkyl, amino-$C_1$-$C_4$-alkyl and amino(hydroxy)$C_1$-$C_4$-alkyl. Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Many of the compounds represented by formula (I) are capable of forming acid addition salts, particularly pharmaceutically acceptable acid addition salts. Pharmaceutically acceptable acid addition salts of the compound of formula (I) include those of inorganic acids, e.g., hydrohalic acids, such as hydrochloric acid or hydrobromic acid; nitric acid; sulphuric acid; phosphoric acid; and organic acids, e.g., aliphatic monocarboxylic acids, such as formic acid, acetic acid, diphenylacetic acid, triphenylacetic acid, caprylic acid, dichloroacetic acid, trifluoroacetic acid, hippuric acid, propionic acid and butyric acid; aliphatic hydroxy acids, such as lactic acid, citric acid, gluconic acid, mandelic acid, tartaric acid or malic acid; dicarboxylic acids, such as adipic acid, aspartic acid, fumaric acid, glutamic acid, maleic acid, malonic acid, sebacic acid or succinic acid; aromatic carboxylic acids, such as benzoic acid, p-chlorobenzoic acid, or nicotinic acid; aromatic hydroxy acids, such as o-hydroxybenzoic acid, p-hydroxybenzoic acid, 1-hydroxynaphthalene-2-carboxylic acid or 3-hydroxynaphthalene-2-carboxylic acid; and sulfonic acids, such as ethanesulfonic acid, ethane-1,2-disulfonic acid, 2-hydroxyethanesulfonic acid, methanesulfonic acid, (+)-camphor-10-sulfonic acid, benzenesulfonic acid, naphthalene-2-sulfonic acid, naphthalene-1,5-disulfonic acid or p-toluenesulfonic acid. These salts may be prepared from compounds of formula (I) by known salt-forming procedures.

Compounds of formula (I) which contain acidic, e.g., carboxyl, groups, are also capable of forming salts with bases, in particular, pharmaceutically acceptable bases, such as those well-known in the art; suitable such salts include metal salts, particularly, alkali metal or alkaline earth metal salts, such as sodium, potassium, magnesium, calcium or zinc salts; or salts with ammonia or pharmaceutically acceptable organic amines or heterocyclic bases, such as benethamine, benzathine, diethanolamine, ethanolamine, 4(2-hydroxyethyl)morpholine, 1-(2-hydroxyethyl)pyrrolidine, N-methyl glucamine, piperazine, triethanolamine or tromethamine. These salts may be prepared from compounds of formula (I) by known salt-forming procedures.

In those compounds where there is an asymmetric carbon atom or an axis of chirality the compounds exist in individual optically active isomeric forms or as mixtures thereof, e.g., as racemic or diastereomeric mixtures. The present invention embraces both individual optically active R and S isomers, as well as mixtures, e.g., racemic or diastereomeric mixtures thereof.

Specific especially preferred compounds of formula (I) include those hereinafter described in the Examples.

Since prodrugs are known to enhance numerous desirable qualities of pharmaceuticals, e.g., solubility, bioavailability, manufacturing, etc., the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino or sulfhydryl group is bonded to any group that, when the prodrug of the present invention is administered to a mammalian subject, it cleaves to form a free hydroxyl, free amino or free sulfhydryl group, respectively. Examples of prodrugs include, but are not limited to, acetate, formate and benzoate derivatives of alcohol and amine functional groups in the compounds of the present invention.

"Therapeutically effective amount" is intended to include an amount of a compound of the present invention alone or an amount of the combination of compounds claimed or an amount of a compound of the present invention in combination with other active ingredients effective to treat the inflammatory diseases described herein.

As used herein, "treating" or "treatment" cover the treatment of a disease-state in a mammal, particularly in a human, and include:

(a) preventing the disease-state from occurring in a mammal, in particular, when such mammal is predisposed to the disease-state but has not yet been diagnosed as having it;
(b) inhibiting the disease-state, i.e., arresting it development; and/or
(c) relieving the disease-state, i.e., causing regression of the disease state.

Synthesis

Another embodiment of the present invention provides a process for the preparation of compounds of formula (I) in free or pharmaceutically acceptable salt form, which comprises the steps of:

(i) (A) for the preparation of compounds of formula (I), wherein $R^1$ is $R^{1a}S—$, $R^{1a}O—$ or $R^{1a}NR^9$, wherein $R^{1a}$ is

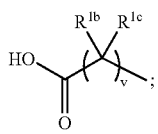

and all other symbols are as hereinbefore defined;
(B) cleaving an ester group —$COOR^8$ in a compound of formula (I), wherein $R^1$ is $R^{1a}S—$, $R^{1a}O—$ or $R^{1a}NR^9$, wherein $R^{1a}$ is

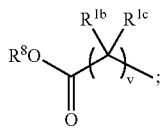

and
$R^8$ is selected from $C_1$-$C_8$-alkyl, $C_3$-$C_{15}$-cycloalkyl, $C_1$-$C_8$-alkyl($C_6$-$C_{15}$-aromatic carbocyclic group), and $C_6$-$C_{15}$-aromatic carboxylic group; and
all other symbols are as hereinbefore defined; and
(ii) recovering the resultant compound of formula (I), in free or pharmaceutically acceptable salt form.

The process for the preparation of compounds of formula (I) may be carried out using known procedures for ester cleavage or analogously as hereinafter described in the Examples.

Starting materials for the process for the preparation of compounds of formula (I), and compounds for the preparation of those starting materials, may be novel or known; they may be prepared in accordance with known procedures or analogously as hereinafter described in the Examples.

The compounds of formula (I) can be prepared, e.g., using the reactions and techniques described below. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5th Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991).

Generally, compounds described in the scope of this patent application can be synthesized by the routes described in Schemes 1 and 2.

In Scheme 1, alkylation of a substituted phenol 1 with a haloacetate ester (preferably methyl bromoacetate) in the presence of an inorganic base generates intermediate 2. Reduction of the aldehyde moiety of intermediate 2 with sodium borohydride provides the alcohol derivative 3. Bromination of alcohol derivative 3 with phosphorus tribromide provides intermediate 4. Next, intermediate 4 is coupled with an aromatic boronic acid using a palladium catalyst to generate intermediate 5. Alkylation of intermediate 5 with a halocarboxylate ester (preferably tert-butyl bromopropionate) yields the tert-butyl ester derivative 6. Subsequent cleavage of the tert-butyl ester affords 7 which can be transformed into a cyclic amide 8 using a cyclic secondary amine and polymer supported carbonyl diimidazole and N-hydroxybenzotriazole in acetonitrile with microwave irradiation according to *Org Lett*, Vol. 5, p. 4721 (2003). Finally hydrolysis provides compound 9.

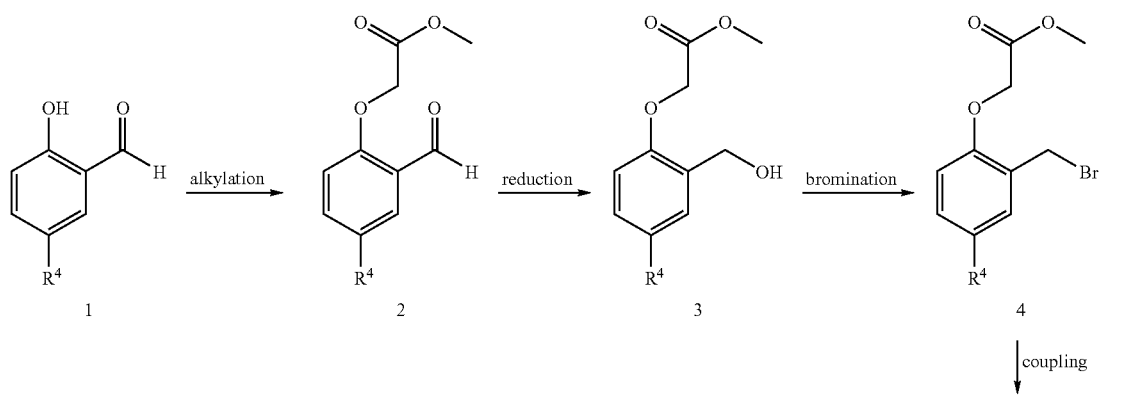
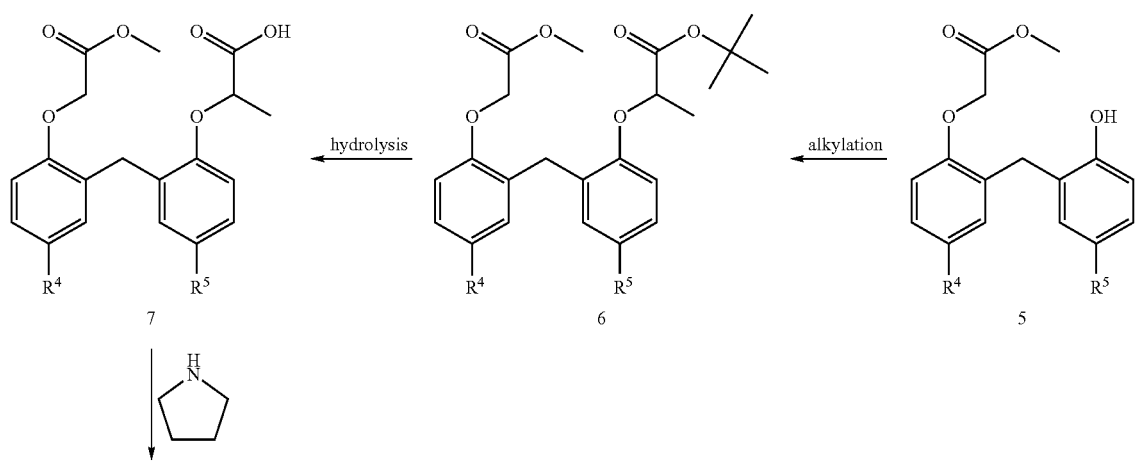
Alternatively, as depicted in Scheme 2, when $R^4$ and $R^5$ are the same, intermediate 10 can be selectively alkylated using a bromoacetate derivative, such as benzyl bromoactetate, according to the procedure of Synlett, p. 199 (2003) to provide intermediate 11. From intermediate 11, intermediates 12, 13, 14 and compound 15 can be generated similar to the procedures described in Scheme 1.

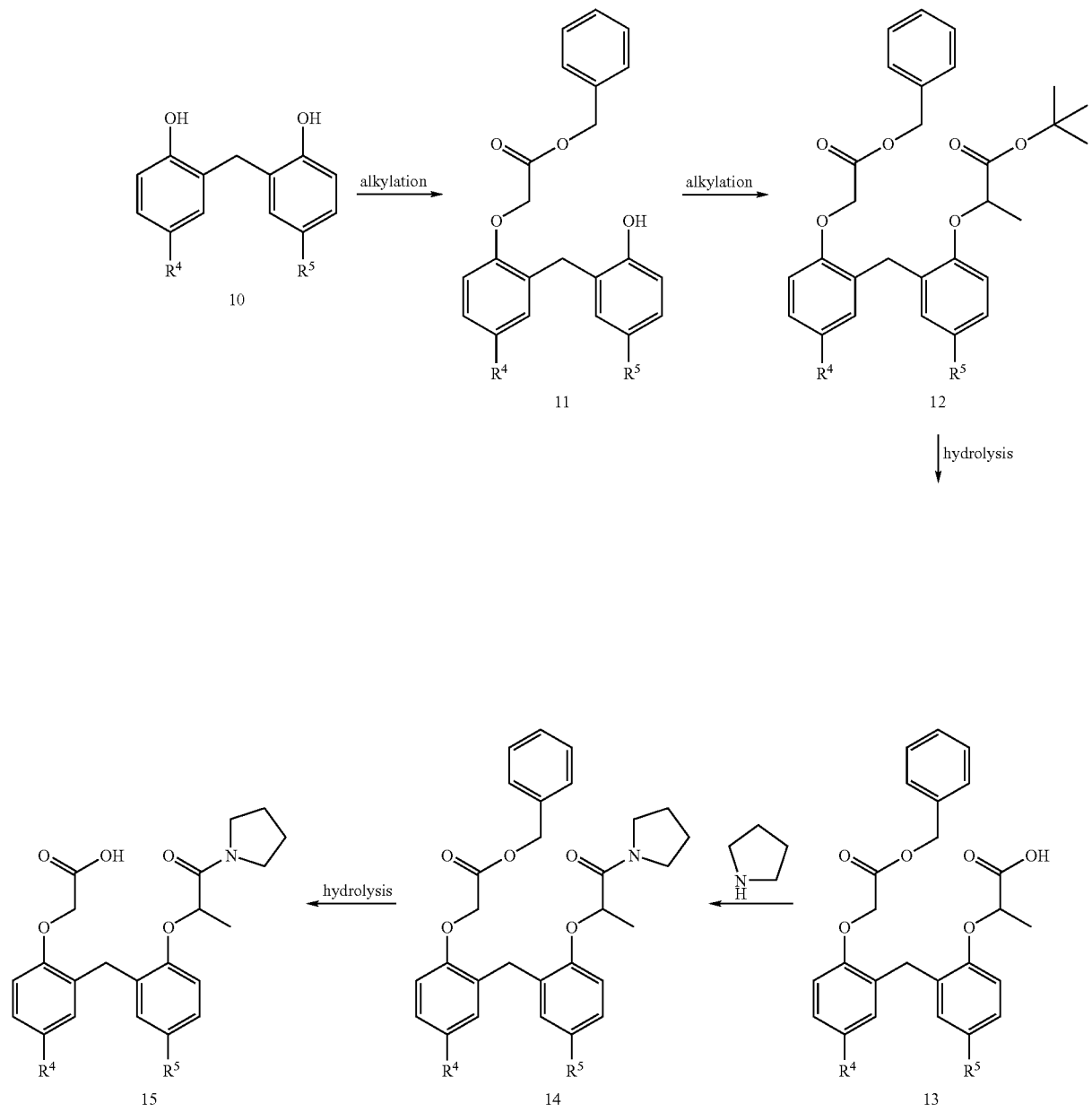

EXAMPLES

Structure for Examples 1–7:

HO-C(=O)-CH2-O-[phenyl(R12)]-X-[phenyl(Y-Q)(R13)]
X = CH2
Y = O

| Example | R12 | R13 | Q | MH+ |
|---|---|---|---|---|
| 1 | Cl | Cl | -CH(CH3)-C(=O)-N(pyrrolidine) | 452 |
| 2 | Cl | Cl | -CH(CH3)-C(=O)-N(pyrrolidine) | 452 (1), 452 (2) |
| 3 | Cl | Cl | -CH(CH3)-C(=O)-N(morpholine) | 468 |
| 4 | Cl | Cl | -CH(CH3)-C(=O)-N(piperidine) | 466 |
| 5 | Cl | H | -CH(CH3)-C(=O)-N(piperazine-CH2CH2CN) | 486 |
| 6 | Cl | H | -CH(CH3)-C(=O)-N(4-methylpiperazine) | 447 |
| 7 | Cl | H | -CH(CH3)-C(=O)-N(pyrrolidine) | 418 |

-continued

X = CH2
Y = O

| Example | R12 | R13 | Q | MH+ |
|---|---|---|---|---|
| 8 | Cl | H | -CH(CH3)-C(=O)-N(pyrrolidine) | 418 (1), 418 (2) |
| 9 | Cl | H | -CH(CH3)-C(=O)-N(piperidine) | 432 |
| 10 | Cl | Cl | -CH(CH3)-C(=O)-N(4-methylpiperazine) | 467 |

General Conditions

LCMS are recorded on an Agilent 1100 LC system with a Waters Xterra MS C18 4.6×100 5 µM column, eluting with 5-95% 10 mM aqueous ammonium bicarbonate in acetonitrile over 2.5 minutes, with negative ion electrospray ionization or 5-95% water+0.1% TFA in acetonitrile with positive ion electrospray ionization. MH+ refer to monoisotopic molecular weights.

Melting points (m.p.) are uncorrected.

NMR are recorded at 400 MHz in CDCl$_3$, unless otherwise noted. The Emrys™ Optimiser microwave instrument (PersonalChemistry AB) is used in the standard configuration as delivered.

| Abbreviations | |
|---|---|
| CHCl$_3$ | chloroform |
| DCM | dichloromethane |
| DIPEA | diisopropylethylamine |
| DMAP | 4-(dimethylamino)pyridine |
| DME | 1,2-dimethoxyethane |
| DMF | dimethylformamide |
| EtOAc | ethyl acetate |
| HATU | O-(7-azabenzotriazol-1-yl)-N,N,N',N'-tetramethyluronium hexafluorophophate |
| HCl | hydrochloric acid |
| HOAT | 1-hydroxy-7-azabenzotriazole |
| HOBt | 1-hydroxybenzotriazole |

-continued

| Abbreviations | |
|---|---|
| HPLC | high performance liquid chromatography |
| IPA | iso-propyl alcohol |
| MeOH | methanol |
| $MgSO_4$ | magnesium sulfate |
| $NaHCO_3$ | sodium bicarbonate |
| NaH | sodium hydride |
| NaOH | sodium hydroxide |
| $Na_2SO_4$ | sodium sulfate |
| $Pd(PPh_3)_4$ | tetrakis(triphenylphosphine) palladium(0) |
| PS-CDI | polymer supported carbodiimide |
| PS-EDC | polymer supported 1-(3-dimethylaminopropyl)-3-ethylcarbodiimide |
| RT | room temperature |
| TEA | triethylamine |
| TFA | trifluoroacetic acid |
| THF | tetrahydrofuran |

PREPARATION OF INTERMEDIATES

Intermediate A

2-[2-(2-Benzyloxycarbonylmethoxy-5-chloro-benzyl)-4-chloro-phenoxy]-propionic acid A1) Preparation of [4-chloro-2-(5-chloro-2-hydroxy-benzyl)-phenoxy]-acetic acid benzyl ester 2,2'-Methylene-bis(4-chloro-phenol) (12 g, 44.6 mmol) is dissolved in DMF (100 mL). Lithium carbonate (3.3 g, 44.6 mmol) is added, followed by benzyl-2-bromoacetate (7.7 mL, 49 mmol). The suspension is stirred at 80° C. for 8 hours. Further benzyl-2-bromoacetate (1 mL, 6.4 mmol) is added and stirring continued at 100° C. for 4 hours. The reaction mixture is evaporated to dryness, water is added to the residue which is acidified to pH 1 with 2 M aqueous HCl and extracted with EtOAc. The organic layer is washed with brine, dried ($MgSO_4$) and evaporated. The crude product is purified by flash column chromatography over silica gel eluting with 4:1 iso-hexane:EtOAc. The product is suspended in iso-hexane, dissolved in the minimum volume of EtOAc, seeded and left to stand. The resultant solid is collected by filtration, washed with iso-hexane and dried to give [4-chloro-2-(5-chloro-2-hydroxy-benzyl)-phenoxy]-acetic acid benzyl ester; m.p.=135-137° C.

A2) Preparation of 2-[2-(2-benzyloxycarbonyl-methoxy-5-chloro-benzyl)-4-chloro-phenoxy]-propionic acid tert-butyl ester To a solution of 2-bromopropionic acid tert-butyl ester (0.827 g, 3.95 mmol) in DMF (15 mL) is added [4-chloro-2-(5-chloro-2-hydroxy-benzyl)-phenoxy]-acetic acid benzyl ester (1.5 g, 3.60 mmol) and potassium carbonate (0.547 g, 3.95 mmol). The reaction mixture is stirred at RT overnight and the solvent is removed in vacuo. The crude product is dissolved in EtOAc (50 mL) and washed with water (50 mL) and brine (50 mL). The organic portion is dried ($MgSO_4$) and concentrated in vacuo to yield a yellow oil which is dried in a vacuum oven for 2 hours to afford the titled product which is used in the next step without purification.

A3) Preparation of 2-[2-(2-benzyloxycarbonyl-methoxy-5-chloro-benzyl)-4-chloro-phenoxy]-propionic acid A solution of 2-[2-(2-benzyloxycarbonylmethoxy-5-chloro-benzyl)-4-chloro-phenoxy]-propionic acid tert-butyl ester (1.736 g, 3.18 mmol) in DCM (10 mL) is treated with TFA (5 mL) and allowed to stir at RT for 1 hour. The solvent is removed in vacuo to yield the titled compound as an off-white solid.

Intermediate B

2-[2-(5-Chloro-2-methoxycarbonylmethoxy-benzyl)-phenoxy]-propionic acid

B1) Preparation of (2-bromomethyl-4-chloro-phenoxy)-acetic acid methyl ester

To a cooled (0° C.) solution of (4-chloro-2-hydroxymethyl-phenoxy)-acetic acid methyl ester (5 g, 0.022 mmol) in DCM (50 mL) under an inert atmosphere of nitrogen is added phosphorus tribromide (1.03 mL, 0.011 mol) and the mixture is stirred at 0° C. for 90 minutes. The reaction mixture is diluted with water (15 mL) and allowed to warm to RT. The mixture is then washed with water (2×25 mL) and the organic portion is separated, washed with brine, dried ($MgSO_4$) and concentrated in vacuo to yield the titled compound as a white solid.

B2) Preparation of [4-chloro-2-(2-hydroxy-benzyl)-phenoxy]-acetic acid methyl ester (i) A solution of 2 M $Na_2CO_3$ (70 mL, 0.053 mol) is treated with 2-hydroxyphenyl boronic acid (9.7 g, 0.074 mol) in DME (200 mL). To this mixture is added bis(triphenylphosphine)palladium (II) chloride (3.24 g, 4.72 mmol) followed by (2-bromomethyl-4-chloro-phenoxy)-acetic acid methyl ester in DME (200 mL) and the reaction mixture is heated to reflux overnight. After cooling to RT, the reaction mixture is filtered through Celite® and concentrated in vacuo to yield a 1:1 mixture of [4-chloro-2-(2-hydroxy-benzyl)-phenoxy]-acetic acid and [4-chloro-2-(2-hydroxy-benzyl)-phenoxy]-acetic acid methyl ester.

(ii) A solution comprising a 1:1 mixture of [4-chloro-2-(2-hydroxy-benzyl)-phenoxy]-acetic acid and [4-chloro-2-(2-hydroxy-benzyl)-phenoxy]-acetic acid methyl ester (3.32 g, 0.011 mol—approx.) in methanol (70 mL) is treated dropwise with concentrated sulphuric acid (2.2 mL) and heated to reflux for 2 hours. The mixture is cooled to RT and the solvent is removed in vacuo. The crude product is dissolved in EtOAc (300 mL) and washed with saturated sodium bicarbonate solution (300 mL). The organic layer is separated and the aqueous portion is extracted with EtOAc (200 mL). The organic extracts are combined, washed with water (300 mL), brine (300 mL), dried $MgSO_4$ and concentrated in vacuo to yield a solid which is dried in a vacuum oven at 40° C. to yield the titled product.

B3) Preparation of 2-[(2-(5-chloro-2-methoxycarbonylmethoxy-benzyl)-phenoxy]-propionic acid The titled compound is prepared analogously to 2-[2-(2-benzyloxycarbonylmethoxy-5-chloro-benzyl)-4-chloro-phenoxy]-propionic acid by replacing [4-chloro-2-(5-chloro- 2-hydroxy-benzyl)-phenoxy]-acetic acid benzyl ester with [4-chloro-2-(2-hydroxy-benzyl)-phenoxy]-acetic acid methyl ester.

Intermediate C

The titled compound is prepared analogously to 2-[2-(2-benzyloxycarbonylmethoxy-5-chloro-benzyl)-4-chloro-phenoxy]-propionic acid (Intermediate A) by replacing 2-bromopropionic acid tert-butyl ester with tert-butyl bromoacetate.

EXAMPLE 1

{4-Chloro-2-[5-chloro-2-(1-methyl-2-oxo-2-pyrrolidin-1-yl-ethoxy)-benzyl]-phenoxy}-acetic acid a) Preparation of {4-chloro-2-[5-chloro-2-(1-methyl-2-oxo-2-pyrrolidin-1-yl-ethoxy)-benzyl]-phenoxy}-acetic acid benzyl ester To a suspension of 2-[2-(2-benzyloxycarbonylmethoxy-5-chloro-benzyl)-4-chloro-phenoxy]-propionic acid (Intermediate A) (100 mg, 0.204 mmol), HOBt (27.6 mg, 0.204 mmol) and PS-CDI (326.4 mg, 1.25 mmol/g, 0.408 mmol) in acetonitrile (15 mL) is added pyrrolidine (17.1 µL, 0.204 mmol). The reaction mixture is heated using microwave radiation in a Personal Chemistry Emrys™ Optimizer microwave reactor at 100° C. for 5 minutes. The PS-CDI resin is removed by filtration, rinsing with DCM and MeOH and the filtrate is concentrated in vacuo. The crude product is dissolved in EtOAc (50 mL) and washed with water (50 mL), aqueous sodium carbonate solution (30 mL), brine (50 mL) and then dried ($MgSO_4$). The solvent is removed in vacuo and purification of the crude product by chromatography on silica eluting with EtOAc/iso-hexane (1:4) affords the titled product as a racemic mixture; $MH^+$=542.

b) Preparation of {4-chloro-2-[5-chloro-2-(1-methyl-2-oxo-2-pyrrolidin-1-yl-ethoxy)-benzyl]-phenoxy}-acetic acid A solution comprising {4-chloro-2-[5-chloro-2-(1-methyl-2-oxo-2-pyrrolidin-1-yl-ethoxy)-benzyl]-phenoxy}-acetic acid benzyl ester (63 mg, 0.116 mmol) in MeOH (1 mL) is treated with 2 M NaOH (145 µL) and allowed to stir at RT overnight. The resulting suspension is filtered, dissolved in water (1 mL) and the pH of the solution is adjusted to pH 1 using 2 M HCl. A precipitate forms which is filtered and dried in a vacuum oven to afford the titled product; $MH^+$=452.

EXAMPLE 2

{4-Chloro-2-[5-chloro-2-((R/S)-1-methyl-2-oxo-2-pyrrolidin-1-yl-ethoxy)-benzyl]-phenoxy}-acetic acid—Enantiomer 1 and Enantiomer 2

The enantiomers prepared in Example 1a are resolved using a chiralcel OD column eluting with 30% IPA in hexanes to afford enantiomer A (retention time=8.44 minutes) and enantiomer B (retention time=12.7 minutes). Enantiomer 1 is prepared using an analogous procedure to {4-chloro-2-[5-chloro-2-(1-methyl-2-oxo-2-pyrrolidin-1-yl-ethoxy)-benzyl]-phenoxy}-acetic acid by replacing the racemic mixture of {4-chloro-2-[5-chloro-2-(1-methyl-2-oxo-2-pyrrolidin-1-yl-ethoxy)-benzyl]-phenoxy}acetic acid benzyl ester with enantiomer A; $MH^+$=452. Enantiomer 2 is prepared analogously using the procedure described above by replacing Enantiomer A with Enantiomer B; $MH^+$=452.

EXAMPLES 3 AND 4

These compounds namely,

{4-Chloro-2-[5-chloro-2-(1-methyl-2-morpholin-4-yl-2-oxo-ethoxy)-benzyl]-phenoxy}-acetic acid (Example 3); and {4-Chloro-2-[5-chloro-2-(1-methyl-2-oxo-2-piperidin-1-yl-ethoxy)-benzyl]-phenoxy}-acetic acid (Example 4), are prepared analogously to {4-chloro-2-[5-chloro-2-(1-methyl-2-oxo-2-pyrrolidin-1-yl-ethoxy)-benzyl]-phenoxy}-acetic acid (Example 1) by replacing pyrrolidine with the appropriate cyclic amine.

EXAMPLES 5-7

These compounds namely,

[4-Chloro-2-(2-{2-[4-(2-cyano-ethyl)-piperazin-1-yl]-1-methyl-2-oxo-ethoxy}benzyl)-phenoxy]-acetic acid (Example 5);

(4-Chloro-2-{2-[1-methyl-2-(4-methyl-piperazin-1-yl)-2-oxo-ethoxy]-benzyl}phenoxy)-acetic acid (Example 6); and {4-Chloro-2-[2-(1-methyl-2-oxo-2-pyrrolidin-1-yl-ethoxy)-benzyl]-phenoxy}acetic acid (Example 7), are prepared analogously to Example 1 by replacing 2-[2-(2-benzyloxycarbonylmethoxy-5-chloro-benzyl)-4-chloro-phenoxy]-propionic acid (Intermediate A) with 2-[2-(5-chloro-2-methoxycarbonylmethoxy-benzyl)-phenoxy]-propionic acid (Intermediate B) and by replacing pyrrolidine with the appropriate cyclic amine.

EXAMPLE 8

{4-Chloro-2-[2-((R/S)-1-methyl-2-oxo-2-pyrrolidin-1-yl-ethoxy)-benzyl]-phenoxy}-acetic acid—Enantiomer 1 and Enantiomer 2

These compounds are prepared analogously to Example 2 by chiral resolution of the precursor racemate ({4-chloro-2-[2-(1-methyl-2-oxo-2-pyrrolidin-1-yl-ethoxy)-benzyl]-phenoxy}-acetic acid methyl ester) to produce Enantiomer C (Retention time=5.93 minutes) and Enantiomer D (Retention time=7.66 minutes). Enantiomer C and Enantiomer D are then hydrolyzed using the conditions described in Example 1b to afford Enantiomer 2 and Enantiomer 1, respectively.

EXAMPLE 9

{4-Chloro-2-[2-(1-methyl-2-oxo-2-piperidin-1-yl-ethoxy)-benzyl]-phenoxy}-acetic acid a) Preparation of {4-chloro-2-[2-(1-methyl-2-oxo-2-piperidin-1-yl-ethoxy)-benzyl]-phenoxy}-acetic acid methyl ester To a solution of PS-EDC (0.558 g, 1.42 mmol/g, 0.792 mmol) in DMF (2 mL) is added 2-[2-(5-chloro-2-methoxycarbonylmethoxy-benzyl)-phenoxy]-propionic acid (Intermediate B) (150 mg, 0.396 mmol) in DMF (2 mL) and HOAT (80.8 mg, 0.594 mmol) in DMF (2 mL). The reaction mixture is agitated for 50 minutes and then treated with piperidine (39.2 µL, 0.396 mmol) and agitated at RT for 2 days. Polymer supported trisamine (0.475 g, 1.42 mmol/g, 1.98 mmol) is then added and the mixture is further agitated overnight. The reaction mixture is filtered to remove the resins and rinsed with methanol and DCM. The filtrate is reduced in vacuo and the crude solid is re-dissolved in DCM and washed with water. The organic portion is separated using a phase separator and concentrated in vacuo to yield a solid which is purified by chromatography on silica eluting with EtOAc/iso-hexane (30% increasing to 50% EtOAc) to yield the titled product as a pale yellow oil; $MH^+=446$.

b) Preparation of {4-chloro-2-[2-(1-methyl-2-oxo-2-piperidin-1-yl-ethoxy)-benzyl]-phenoxy}-acetic acid The titled compound is prepared analogously to {4-chloro-2-[5-chloro-2-(1-methyl-2-oxo-2-pyrrolidin-1-yl-ethoxy)-benzyl]-phenoxy}-acetic acid (Example 1) by replacing {4-chloro-2-[5-chloro-2-(1-methyl-2-oxo-2-pyrrolidin-1-yl-ethoxy)-benzyl]-phenoxy}-acetic acid benzyl ester with {4-chloro-2-[2-(1-methyl-2-oxo-2-piperidin-1-yl-ethoxy)-benzyl]-phenoxy}-acetic acid methyl ester; $MH^+=432$.

EXAMPLE 10

(4-Chloro-2-{5-chloro-2-[2-(4-methyl-piperazin-1-yl)-2-oxo-ethoxy]-benzyl}-phenoxy)-acetic acid trifluoroacetate a) Preparation of (4-chloro-2-{5-chloro-2-[2-(4-methyl-piperazin-1-yl)-2-oxo-ethoxy]-benzyl}-phenoxy)-acetic acid benzyl ester To a solution of [2-(2-benzyloxycarbonylmethoxy-5-chloro-benzyl)-4-chloro-phenoxy]-acetic acid (Intermediate C) (0.1 g, 0.211 mmol) in DCM (1 mL) is added DIPEA (37 µL, 0.211 mmol) and HATU (80 mg, 0.211 mmol). After stirring at RT for 1 hour, the reaction mixture is treated with 1-methyl piperidine (24 µL, 0.211 mmol) and allowed to stir at RT for 2 days. The resulting solution is purified by chromatography on silica eluting with EtOAc/MeOH (95:5) to yield the titled product.

b) Preparation of (4-chloro-2-{5-chloro-2-[2-(4-methyl-piperazin-1-yl)-2-oxo-ethoxy]-benzyl}-phenoxy)-acetic acid trifluoroacetate To a solution of (4-chloro-2-{5-chloro-2-[2-(4-methyl-piperazin-1-yl)-2-oxo-ethoxy]-benzyl}-phenoxy)-acetic acid benzyl ester (76 mg, 0.137 mmol) in MeOH (1 mL) is added 2 M NaOH (137 µL) and the reaction mixture is stirred at RT for 3 days. The solvent is removed in vacuo and the resulting crude product is dissolved in water (5 mL). The pH of the solution is adjusted by addition of HCl to form a precipitate which is purified by preparative HPLC to afford the titled product; $MH^+=467$.

Pharmaceutical Use and Assay

Compounds of formula (I) and (Ia) and their pharmaceutically acceptable salts, hereinafter referred to alternatively as "agents of the invention", are useful as pharmaceuticals. In particular, the compounds have good $CRTh_2$ receptor antagonist activity and may be tested in the following assays.

Filtration Binding Assay Protocol

The binding of $CRTh_2$ antagonists is determined using membranes prepared from human $CRTh_2$-expressing Chinese Hamster Ovary cells (CHO.K1-$CRTh_2$). To produce cell membranes CHO.K1-$CRTh_2$ cells cultured in roller bottles are harvested using cell dissociation buffer (Invitrogen). The cells are pelleted by centrifugation (167 g, 5 minutes). The cell pellet is incubated in hypotonic buffer (15 mM Tris-OH, 2 mM $MgCl_2$, 0.3 mM EDTA, 1 mM EGTA, 1× Complete™ tablet) at 4° C. for 30 minutes. At 4° C. cells are homogenized using a Polytron® (IKA Ultra Turrax T25) for 5 bursts of 1 second. The homogenate is centrifuged (Beckman Optima TM TL Ultracentrifuge, 48,000 g, 30 minutes at 4° C.). The supernatant is discarded and the membrane pellet re-suspended in homogenisation buffer (75 mM Tris-OH, 12.5 mM $MgCl_2$, 0.3 mM EDTA, 1 mM EGTA, 250 mM Sucrose, 1× Complete™ tablet. Membrane preparations are aliquoted and stored at 80° C. The protein content is estimated using Bradford Protein Assay Dye (Bio Rad).

The binding of [$^3$H]-$PGD_2$ (157 Ci/mmol) to CHO.K1-$CRTh_2$ membranes is determined in the absence (total binding) and presence (non-specific binding) of unlabelled $PGD_2$ (1 µM). Subtraction of the cpm (counts per minute) of [$^3$H]-$PGD_2$ binding in presence of excess unlabelled $PGD_2$ from that observed in the absence of excess unlabelled $PGD_2$ is defined as specific binding. Active $CRTh_2$ antagonists are able to compete with [$^3$H]-$PGD_2$ for binding to the $CRTh_2$ receptor and are identified in a decrease in the number of cpm bound.

The assay is performed in Greiner U-bottomed 96 well-plates, in a final volume of 100 µL/well. CHO.K1-$CRTh_2$ membranes were diluted in assay buffer (10 mM HEPES-KOH (pH 7.4), 1 mM EDTA and 10 mM $MnCl_2$) and 10 µµg are added to each well. [$^3$H]-$PGD_2$ is diluted in assay buffer and added to each well at a final concentration of 2.5 nM. To determine non-specific binding, [3H]-$PGD_2$ binding to the CRTh2 receptor is competed with using unlabelled $PGD_2$ at a final well concentration of 1 µM. The experiment is done in triplicate, with reagents added to the wells as follows:

25 µL assay buffer for total binding or
25 µL $PGD_2$ to determine non-specific binding
25 µL [$^3$H]$PGD_2$
50 µL membranes
25 µL test compound in DMSO/assay buffer The plates are incubated at RT on a shaker for 1 hour, and then harvested (Tomtec Harvester 9600) onto GF/C filter plates using wash buffer (10 mM HEPES-KOH, pH 7.4). The plate is dried for 2 hours, prior to addition of Micro-Scint 20™ (50 µL) and sealing with TopSeal-S™. Plates are then counted using a Packard Top Count instrument, Plates are then read on the Packard Topcount with the 3H Scintillation program (1 minute/well).

Ki (dissocation constant for the inhibition) values for the $CRTh_2$ antagonists are reported. Ki values are determined using Sigma Plot™ software, using the Cheng-Prussoff equation.

$$Ki=IC_{50}/1+[S]/Kd,$$

where S is the concentration of radioligand and Kd is the dissociation constant.

$CRTH_2$ cAMP Functional Assay Protocol

This assay is conducted in CHO.K1-$CRTh_2$ cells. cAMP is generated in the cell by stimulating cells with 5 µM forskolin, an adenylate cyclase activator. $PGD_2$ is added to activate the $CRTh_2$ receptor which results in the attenuation of the forskolin-induced cAMP accumulation. Potential CRTh2 antagonists are tested for their ability to inhibit the $PGD_2$-mediated attenuation of the forskolin-induced cAMP accumulation in CHO.K1-$CRTh_2$ cells.

For each concentration value on the dose-response curve, test compounds are prepared in assay stimulation buffer (HBSS, 5 mM HEPES, 10 µM IBMX±0.1% human serum albumin) containing DMSO (3% vol/vol) and 5 µL/well is added to an assay plate (384-well white optiplate).

CHO.K1-CRTh$_2$ cultured in tissue culture flasks are washed with PBS and harvested with dissociation buffer. Cells are washed with PBS and resuspended in stimulation buffer to a concentration of 0.4×10$^6$/mL and added to the assay plate (10 µL/well).

The assay plate is incubated at room temperature on a shaker for 15 minutes.

A mix of agonist (10 nM Prostaglandin D$_2$) and 5 µM forskolin is prepared in assay stimulation buffer and added to the assay plate (5 µL/well).

In addition, a cAMP standard is serially diluted in assay stimulation buffer and added to separate empty wells on the assay plate (20 µL/well). The cAMP standard allows for the quantification of cAMP generated in CHO.K1-CRTH$_2$ cells.

The assay plate is incubated at room temperature on a shaker for 60 minutes.

Cell lysis buffer (Lysis buffer: Milli-Q H$_2$O, 5 mM HEPES, 0.3% Tween-20, 0.1% human serum albumin) is added to a bead mix (containing Alphascreen™ anti-cAMP acceptor beads 0.06 units/µL, Alphascreen™ streptavidin-coated donor beads 0.06 units/µL, biotinylated cAMP 0.06 units/µL, 10 µM IBMX) is prepared under darkened conditions 60 minutes prior to addition to the assay plate. The resulting lysis mix is added to all wells of the assay plate (40 µL/well).

The assay plate is sealed with Topseal-S™ and incubated in the dark at room temperature on a shaker for 45 minutes. The plate is then counted using a Packard Fusion™ instrument.

The resulting counts per minute are converted to nM cAMP by using the prepared cAMP standard curve. IC$_{50}$ values (concentration of CRTh2 antagonist required to inhibit 50% of the PGD$_2$-mediated attenuation of forskolin-induced cAMP accumulation in CHO.K1-CRTh$_2$ cells) are then determined using Prism™ software.

Compounds of the Examples herein generally have Ki values in the SPA binding assay below 1 µM. The compounds also generally have IC$_{50}$ values in the functional assays below 1 µM.

Compounds of the Examples herein below generally have Ki values in the SPA binding assay below 1 µM. For example, the compounds of Examples 1, 3, 7 and 8 (enantiomer 1) have Ki values of 0.0403, 0.0950 0.0824 and 0.0602 µM, respectively.

Compounds of the Examples herein below generally have IC$_{50}$ values in the functional assay below 1 µM. For example, the compounds of Examples 1, 3, 7 and 8 (enantiomer 1) have IC$_{50}$ values of 0.0225, 0.0225 0.0375 and 0.0250 µM, respectively.

Compounds of formula (I) and (Ia), in free or salt form, are antagonists of the G-protein-coupled chemoattractant receptor CRTh$_2$, expressed on Th$_2$ cells, eosinophils and basophils. PGD$_2$ is the natural ligand for CRTh$_2$. Thus, antagonists which inhibit the binding of CRTh$_2$ and PGD$_2$ are useful in the treatment of allergic and anti-inflammatory conditions. Treatment in accordance with the invention may be symptomatic or prophylactic.

Accordingly, agents of the invention are useful in the treatment of inflammatory or obstructive airways diseases, resulting, e.g., in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitis asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., corticosteroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 a.m., i.e., at a time normally substantially distant from any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis including, e.g., aluminosis, anthracosis, asbestosis, chalicosis, ptilosis, siderosis, silicosis, tabacosis and byssinosis.

Having regard to their anti-inflammatory activity, in particular, in relation to inhibition of eosinophil activation, agents of the invention are also useful in the treatment of eosinophil related disorders, e.g., eosinophilia, in particular, eosinophils-related disorders of the airways, e.g., involving morbid eosinophilic infiltration of pulmonary tissues including hypereosinophilia as it effects the airways and/or lungs, as well as, e.g., eosinophil-related disorders of the airways consequential or concomitant to Löffler's syndrome; eosinophilic pneumonia; parasitic, in particular, metazoan, infestation including tropical eosinophilia; bronchopulmonary aspergillosis; polyarteritis nodosa including Churg-Strauss syndrome; eosinophilic granuloma; and eosinophil-related disorders affecting the airways occasioned by drug-reaction.

Agents of the invention are also useful in the treatment of inflammatory or allergic conditions of the skin, e.g., psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita and other inflammatory or allergic conditions of the skin.

Agents of the invention may also be used for the treatment of other diseases or conditions, in particular, diseases or conditions having an inflammatory component, e.g., treatment of diseases and conditions of the eye, such as conjunctivitis, keratoconjunctivitis sicca and vernal conjunctivitis; diseases affecting the nose including allergic rhinitis; and inflammatory disease, in which autoimmune reactions are implicated or having an autoimmune component or aetiology, including autoimmune hematological disorders, e.g., hemolytic anemia, aplastic anaemia, pure red cell anaemia and idiopathic thrombocytopenia; systemic lupus erythematosus; polychondritis; sclerodoma; Wegener granulamatosis; dermatomyositis; chronic active hepatitis; myasthenia gravis; Steven-Johnson syndrome; idiopathic sprue; autoimmune inflammatory bowel disease, e.g., ulcerative colitis and Crohn's disease; endocrine opthalmopathy; Grave's disease; sarcoidosis; alveolitis; chronic hypersensitivity pneumonitis; multiple sclerosis; primary billiary cirrhosis; uveitis (anterior and posterior); keratoconjunctivitis sicca and vernal keratoconjunctivitis; interstitial lung fibrosis; psoriatic arthritis; and glomerulonephritis, with and without nephrotic syndrome, e.g., including idiopathic nephrotic syndrome or minal change nephropathy.

Other diseases or conditions which may be treated with agents of the invention include septic shock; rheumatoid arthritis; osteoarthritis; proliferative diseases, such as cancer; atherosclerosis; allograft rejection following transplantation; stroke; obesity; restenosis; diabetes, e.g., diabetes mellitus type I (juvenile diabetes) and diabetes mellitus type II; diarrheal diseases; ischemia/reperfusion injuries; retinopathy, such as diabetic retinopathy or hyperbaric oxygen-induced retinopathy; and conditions characterized by elevated intraocular pressure or secretion of ocular aqueous humor, such as glaucoma.

The effectiveness of an agent of the invention in inhibiting inflammatory conditions, e.g., in inflammatory airways diseases, may be demonstrated in an animal model, e.g., a mouse or rat model, of airways inflammation or other inflammatory conditions, e.g., as described by Szarka et al., *J Immunol Methods*, Vol. 202, pp. 49-57 (1997); Renzi et al., *Am Rev Respir Dis*, Vol. 148, pp. 932-939 (1993); Tsuyuki et al., *J Clin Invest*, Vol. 96, pp. 2924-2931 (1995); Cernadas et al., *Am J Respir Cell Mol Biol*, Vol. 20, pp. 1-8 (1999); and Williams and Galli, *J Exp Med*, Vol. 192, pp. 455-462 (2000).

The agents of the invention are also useful as co-therapeutic agents for use in combination with other drug substances, such as anti-inflammatory, bronchodilatory or antihistamine drug substances, particularly in the treatment of obstructive or inflammatory airways diseases, such as those mentioned hereinbefore, e.g., as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Such anti-inflammatory drugs include steroids, in particular, glucocorticosteroids, such as budesonide, beclamethasone dipropionate, fluticasone propionate, ciclesonide or mometasone furoate; or steroids, described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445 and WO 03/072592, WO 04/039827, WO 04/066920; non-steroidal glucocorticoid receptor agonists, such as those described in WO 00/00531, WO 02/10143 DE 10261874 (2004), WO 03/082280, WO 03/082787, WO 03/104195, WO 03/101932, WO 04/019935, WO 04/018429, WO 04/005229, WO 03//086294 and WO 04/26248; LTB4 antagonists, such as those described in U.S. Pat. No. 5,451,700; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene), SelCID(TM) CC-10004 (Celgene), KW4490 (Kyowa Hakko Kogyo), WO 03/104204, WO 03/104205, WO 04/000814, WO 04/000839 and WO 04/005258 (Merck), as well as those described in WO 98/18796 and WO 03/39544; A2a agonists, such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462 and WO 03/086408; A2b antagonists, such as those described in WO 02/42298; and beta (β)-2-adrenoceptor agonists, such as albuterol (salbutamol), metaproterenol, terbutaline, salmeterol, fenoterol, procaterol, and especially, formoterol and pharmaceutically acceptable salts thereof, and compounds (in free or salt or solvate form) of formula (I) of WO 00/75114, which document is incorporated herein by reference, preferably compounds of the Examples thereof, especially a compound of formula

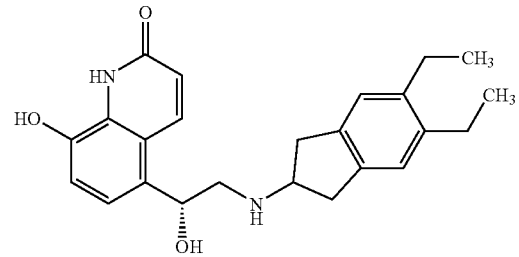

and pharmaceutically acceptable salts thereof, as well as compounds (in free or salt or solvate form) of formula (I) of WO 04/16601. Further-2-adrenoreceptor agonists include compounds of JP 05025045, WO 93/18007, WO 99/64035, US 2002/0055651, WO 01/42193, WO 01/83462, WO/02 66422, WO 02/70490, WO 02/76933, WO 03/024439, WO 03/072539, WO 03/042160, WO 03/091204, WO 03/042164, WO 03/099764, WO 04/016578, WO 04/022547, WO 04/032921, WO 04/037773, WO 04/037807, WO 04/039762, WO 04/039766, WO 04/045618, WO 04/046083, WO 04/033412, WO 04/037768, WO 04/037773 and EP 1440966.

Such bronchodilatory drugs include anticholinergic or antimuscarinic agents, in particular, ipratropium bromide, oxitropium bromide, tiotropium salts and CHF 4226 (Chiesi), but also those described in WO 01/04118, WO 02/51841, WO 02/53564, WO 03/00840, WO 03/87094, WO 04/05285, WO 02/00652, WO 03/53966, EP 0424021, U.S. Pat. No. 5,171, 744, U.S. Pat. No. 3,714,357 and WO 03/33495.

Such co-therapeutic antihistamine drug substances include cetirizine hydrochloride, acetaminophen, clemastine fumarate, promethazine, loratidine, desloratidine, diphenhydramine and fexofenadine hydrochloride.

Combinations of agents of the invention and steroids, β-2 agonists, PDE4 inhibitors or LTD4 antagonists may be used, e.g., in the treatment of COPD or, particularly, asthma. Combinations of agents of the invention and anticholinergic or antimuscarinic agents, PDE4 inhibitors, dopamine receptor agonists or LTB4 antagonists may be used, e.g., in the treatment of asthma or, particularly, COPD.

Other useful combinations of agents of the invention with anti-inflammatory drugs are those with antagonists of chemokine receptors, e.g., CCR-1, CCR-2, CCR-3, CCR-4, CCR-5, CCR-6, CCR-7, CCR-8, CCR-9, CCR-10, CXCR1, CXCR2, CXCR3, CXCR4 and CXCR5; particularly useful are CCR-3 antagonists, such as those described in WO 2002/026723, especially 4-{3-[(S)-4-(3,4-dichlorobenzyl)-morpholin-2-ylmethyl]-ureidomethyl}-benzamide and those described in WO 2003/077907, WO 2003/007939 and WO 2002/102775.

Also especially useful are CCR-5 antagonists, such as Schering-Plough antagonists SC-351125, SCH-55700 and SCH-D; Takeda antagonists, such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770); and CCR-5 antagonists, described in U.S. Pat. No. 6,166,037, WO 00/66558 and WO 00/66559.

The agents of the invention may be administered by any appropriate route, e.g., orally, e.g., in the form of a tablet or capsule; parenterally, e.g., intravenously; by inhalation, e.g., in the treatment of inflammatory or obstructive airways disease; intranasally, e.g., in the treatment of allergic rhinitis; topically to the skin, e.g., in the treatment of atopic dermatitis; or rectally, e.g., in the treatment of inflammatory bowel disease.

The present invention also provides a pharmaceutical composition comprising a compound of formula (I) in free form or in the form of a pharmaceutically acceptable salt, optionally together with a pharmaceutically acceptable diluent or carrier therefore. The composition may contain a co-therapeutic agent, such as an anti-inflammatory, bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

The present invention also provides for the use of a compound of the present invention in any of the aforementioned embodiments, in free or pharmaceutically acceptable salt form, for the manufacture of a medicament for the treatment of an inflammatory or allergic condition, particularly an inflammatory or obstructive airways disease.

The present invention also provides a method for treating or preventing inflammatory or allergic conditions comprising administering to a patient in need thereof a therapeutically effective amount of a compound of the present invention, in free or a pharmaceutically acceptable salt form.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight); and/or one or more surfactants, such as oleic acid or sorbitan trioleate; and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture. When the composition comprises a nebulized formulation, it preferably contains, e.g., the compound of formula (I) either dissolved, or suspended, in a vehicle containing water, a co-solvent, such as ethanol or propylene glycol and a stabilizer, which may be a surfactant.

The invention includes:
(a) an agent of the invention in inhalable form, e.g., in an aerosol or other atomizable composition or in inhalable particulate, e.g., micronized form;
(b) an inhalable medicament comprising an agent of the invention in inhalable form;
(c) a pharmaceutical product comprising such an agent of the invention in inhalable form in association with an inhalation device; and
(d) an inhalation device containing an agent of the invention in inhalable form.

Dosages of agents of the invention employed in practicing the present invention will of course vary depending, e.g., on the particular condition to be treated, the effect desired and the mode of administration. In general, suitable daily dosages for oral administration are of the order of 0.01-100 mg/kg.

The invention claimed is:
1. A compound of formula (I)

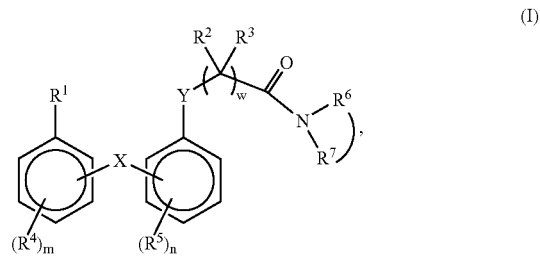

in free or pharmaceutically acceptable salt form,
wherein
$R^1$ is selected from $R^{1a}S—$, $R^{1a}O—$ and $R^{1a}NR^9—$, wherein $R^{1a}$ is

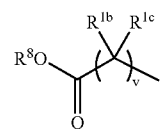

wherein
$R^{1b}$ and $R^{1c}$ are independently selected from H, $C_1$-$C_8$-alkyl, and together with the carbon atom to which they are attached form a divalent $C_3$-$C_8$-cycloaliphatic group;
$R^2$ and $R^3$ are independently selected from H, $C_1$-$C_8$-alkyl, and together with the carbon atom to which they are attached form a divalent $C_3$-$C_8$-cycloaliphatic group;
$R^4$ and $R^5$ are independently selected from H, halogen, $C_1$-$C_8$-alkyl, $C_1$-$C_8$-haloalkyl, a $C_3$-$C_{15}$-carbocyclic group, nitro, cyano, $SO_2R^{5a}$, $C_1$-$C_8$-alkylcarbonyl, $C_1$-$C_8$-alkoxycarbonyl, $C_1$-$C_8$-alkoxy, $C_1$-$C_8$-haloalkoxy, $—SR^{5b}$, carboxy, carboxy-$C_1$-$C_8$-alkyl, amino, amino($C_1$-$C_8$-alkyl), $C_1$-$C_8$-alkylamino($C_1$-$C_8$-alkyl), di($C_1$-$C_8$-alkyl)amino($C_1$-$C_8$-alkyl), $C_1$-$C_8$-alkylamino, di($C_1$-$C_8$-alkyl)amino, $SO_2NR^{5c}R^{5d}$, $C(O)NR^{5e}R^{5f}$, $C_1$-$C_8$-hydroxyalkyl, $NR^{5g}SO_2R^{5h}$, $NR^{5i}(CO)R^{5j}$, $SOR^{5k}$, a $C_6$-$C_{15}$ aromatic carbocyclic group and a 4- to 10-membered heterocyclic group having one or more heteroatoms selected from the group consisting of oxygen, nitrogen and sulphur;

$R^{5a}$, $R^{5k}$ and $R^{5b}$ are independently selected from $C_1$-$C_8$-alkyl, $C_1$-$C_8$-hydroxyalkyl, $C_1$-$C_8$ alkylamino($C_1$-$C_8$-alkyl), di($C_1$-$C_8$-alkyl)amino($C_1$-$C_8$-alkyl), $C_1$-$C_8$-cyanoalkyl, a $C_3$-$C_{15}$-carbocyclic group, $C_1$-$C_8$-haloalkyl and a 4- to 10-membered heterocyclic group having one or more heteroatoms selected from the group consisting of oxygen, nitrogen and sulphur;

$R^{5c}$, $R^{5d}$, $R^{5e}$ and $R^{5f}$ are, independently, H, $C_1$-$C_8$-alkyl, $C_1$-$C_8$-hydroxyalkyl, $C_1$-$C_8$-alkylamino($C_1$-$C_8$-alkyl), di($C_1$-$C_8$-alkyl)amino($C_1$-$C_8$-alkyl), $C_1$-$C_8$-cyanoalkyl, a $C_3$-$C_{15}$-carbocyclic group, $C_1$-$C_8$-haloalkyl, a 4- to 10-membered heterocyclic group having one or more heteroatoms selected from the group consisting of oxygen, nitrogen and sulphur, or, together with the nitrogen atom to which they are attached, form a $C_4$-$C_{10}$-heterocyclic group;

$R^{5g}$ and $R^{5i}$ are independently selected from H, $C_1$-$C_8$-alkyl, $C_1$-$C_8$-hydroxyalkyl, $C_1$-$C_8$-alkylamino($C_1$-$C_8$-alkyl), di($C_1$-$C_8$-alkyl)amino($C_1$-$C_8$-alkyl), $C_1$-$C_8$-cyanoalkyl, a $C_3$-$C_{15}$-carbocyclic group, $C_1$-$C_8$-haloalkyl and a 4- to 10-membered heterocyclic group having one or more heteroatoms selected from the group consisting of oxygen, nitrogen and sulphur;

$R^{5h}$ and $R^{5j}$ are independently selected from $C_1$-$C_8$-alkyl, a $C_3$-$C_{15}$-carbocyclic group, a 4- to 10-membered heterocyclic group having one or more heteroatoms selected from the group consisting of oxygen, nitrogen and sulphur, $C_1$-$C_8$-hydroxyalkyl, amino ($C_1$-$C_8$-alkyl), $C_1$-$C_8$-alkylamino($C_1$-$C_8$-alkyl), di($C_1$-$C_8$-alkyl)amino($C_1$-$C_8$-alkyl) and $C_1$-$C_8$-cyanoalkyl;

$R^6$ and $R^7$, together with the nitrogen to which they are attached form, a 4- to 10-membered heterocyclic group containing the indicated nitrogen atom as a ring heteroatom and optionally at least one ring heteroatom selected from the group consisting of nitrogen, oxygen and sulphur, which ring is unsubstituted or substituted by $C_1$-$C_4$-alkyl, cyano-$C_1$-$C_4$-alkyl, $C_1$-$C_8$-alkylamino or di($C_1$-$C_8$-alkylamino);

$R^8$ is selected from H, $C_1$-$C_8$-alkyl, $C_3$-$C_{15}$-cycloalkyl, $C_1$-$C_8$-alkyl($C_6$-$C_{15}$-aromatic carbocyclic group) and $C_6$-$C_{15}$-aromatic carbocyclic group;

$R^9$ is selected from H, $C_1$-$C_8$-alkyl, $C_3$-$C_{15}$-cycloalkyl, $C_1$-$C_8$-alkyl($C_6$-$C_{15}$-aromatic carbocyclic group), and $C_6$-$C_{15}$-aromatic carbocyclic group;

X is —$CH_2$—, —CH($C_1$-$C_8$-alkyl)-, —CO—, —CH(O$C_1$-$C_8$-alkyl)-, —C(halogen)$_2$-, —O—, —S—, —SO— or, —$SO_2$—;

Y is —O—, —S—, —$CH_2$— or —$NR^7$($C_1$-$C_8$-alkyl)-;
m and n are each, independently, an integer selected from 0-3;
v is an integer selected from 1-3; and
w is an integer selected from 0-3.

2. A compound of formula (I) according to claim 1, in free or pharmaceutically acceptable salt form, wherein $R^1$ is $R^{1a}O$—, where $R^{1a}$ is

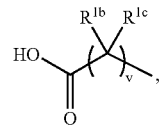

wherein $R^{1b}$ and $R^{1c}$ are H;
$R^2$ and $R^3$ are, independently, H or $C_1$-$C_8$-alky;
$R^6$ and $R^7$, together with the nitrogen to which they are attached, form a 4- to 10-membered heterocyclic group containing the indicated nitrogen atom as a ring heteroatom and optionally at least one ring heteroatom selected from the group consisting of nitrogen, oxygen and sulphur, which ring is unsubstituted or substituted by $C_1$-$C_4$-alkyl, cyano-$C_1$-$C_4$-alkyl, $C_1$-$C_8$-alkylamino or di($C_1$-$C_8$-alkylamino);
$R^{12}$ and $R^{13}$ are, independently, H, or halogen;
X is —$CH_2$—, —S—, —SO— or —$SO_2$—;
Y is —O—;
m and n are 1;
v is 1; and
w is an integer selected from 0-3.

3. A compound according to claim 1 in free or pharmaceutically acceptable salt form, wherein the compound is of formula (Ia)

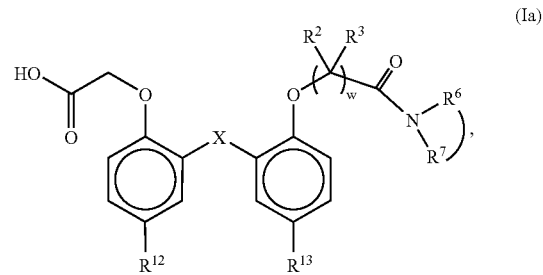

(Ia)

wherein
$R^2$ and $R^3$ are, independently, H or $C_1$-$C_8$-alkyl;
$R^6$ and $R^7$, together with the nitrogen to which they are attached, form a 4- to 10-membered heterocyclic group containing the indicated nitrogen atom as a ring heteroatom and optionally at least one ring heteroatom selected from the group consisting of nitrogen, oxygen and sulphur, which ring is unsubstituted or substituted by $C_1$-$C_4$-alkyl or cyano-$C_1$-$C_4$-alkyl;
X is —$CH_2$—, —S—, —SO— or —$SO_2$—;
$R^{12}$ and $R^{13}$ are, independently, H, or halogen; and
w is 1.

4. A compound according to claim 1 selected from:
{4-Chloro-2-[5-chloro-2-(1-methyl-2-oxo-2-pyrrolidin-1-yl-ethoxy)-benzyl]-phenoxy}-acetic acid;
{4-Chloro-2-[5-chloro-2-((R/S)-1-methyl-2-oxo-2-pyrrolidin-1-yl-ethoxy)-benzyl]-phenoxy}-acetic acid;
{4-Chloro-2-[5-chloro-2-(1-methyl-2-morpholin-4-yl-2-oxo-ethoxy)-benzyl]-phenoxy}-acetic acid;
{4-Chloro-2-[5-chloro-2-(1-methyl-2-oxo-2-piperidin-1-yl-ethoxy)-benzyl]-phenoxy}-acetic acid;
[4-Chloro-2-(2-{2-[4-(2-cyano-ethyl)-piperazin-1-yl-1-methyl-2-oxo-ethoxy}-benzyl)-phenoxy]-acetic acid;
(4-Chloro-2-{2-[1-methyl-2-(4-methyl-piperazin-1-yl)-2-oxo-ethoxy]-benzyl}-phenoxy)-acetic acid;

{4-Chloro-2-[2-(1-methyl-2-oxo-2-pyrrolidin-1-yl-ethoxy)-benzyl]-phenoxy}-acetic acid;
{4-Chloro-2-[2-((R/S)-1-methyl-2-oxo-2-pyrrolidin-1-yl-ethoxy)-benzyl]-phenoxy}-acetic acid;
{4-Chloro-2-[2-(1-methyl-2-oxo-2-piperidin-1-yl-ethoxy)-benzyl]-phenoxy}-acetic acid; and
(4-Chloro-2-{5-chloro-2-[2-(4-methyl-piperazin-1-yl)-2-oxo-ethoxy]-benzyl}-phenoxy)-acetic acid trifluoroacetate.

5. A compound according to claim 1 for use as a pharmaceutical.

6. Pharmaceutical compositions comprising a compound according to claim 1.

7. A process for the preparation of compounds of formula (I) as defined in claim 1, in free or pharmaceutically acceptable salt form, wherein $R^1$ is $R^{1a}S-$, $R^{1a}O-$ or $R^{1a}NR^9$, wherein $R^{1a}$ is

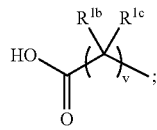

and all other symbols are as hereinbefore defined; which comprises the steps of:

cleaving an ester group $-COOR^8$ in a compound of formula (I), wherein $R^{1a}$ is $R^{1a}S-$, $R^{1a}O-$ or $R^{1a}NR^9$,
wherein $R^{1a}$ is

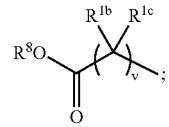

and $R^8$ is selected from $C_1$-$C_8$-alkyl, $C_3$-$C_5$-cycloalkyl, $C_1$-$C_8$-alkyl($C_6$-$C_{15}$-aromatic carbocyclic group) and $C_6$-$C_{15}$-aromatic carboxylic group; and all other symbols are as hereinbefore defined; and (ii) recovering the resultant compound of formula (I), in free or pharmaceutically acceptable salt form.

* * * * *